(12) United States Patent
Tissot et al.

(10) Patent No.: US 7,964,771 B2
(45) Date of Patent: Jun. 21, 2011

(54) TRANSPLASTOMIC PLANTS FREE OF THE SELECTABLE MARKER GENE

(75) Inventors: Ghislaine Tissot, Rillieux-la-Pape (FR); Manuel Dubald, Saint Didier Au Mont D'or (FR); Jean-Marc Ferullo, Covnine (FR)

(73) Assignee: Bayer Crop Science AG (FR)

( * ) Notice: Subject to any disclaimer, the term of this patent is extended or adjusted under 35 U.S.C. 154(b) by 651 days.

(21) Appl. No.: 11/794,753

(22) PCT Filed: Jan. 3, 2006

(86) PCT No.: PCT/EP2006/000731
§ 371 (c)(1),
(2), (4) Date: Jan. 29, 2008

(87) PCT Pub. No.: WO2006/072607
PCT Pub. Date: Jul. 13, 2006

(65) Prior Publication Data
US 2008/0282429 A1  Nov. 13, 2008

Related U.S. Application Data

(60) Provisional application No. 60/683,563, filed on May 23, 2005.

(30) Foreign Application Priority Data

Jan. 5, 2005 (FR) .................... 05 00052

(51) Int. Cl.
*C12N 15/82* (2006.01)
*A01H 5/00* (2006.01)

(52) U.S. Cl. ...................... 800/298; 800/278

(58) Field of Classification Search ............ None
See application file for complete search history.

(56) References Cited

U.S. PATENT DOCUMENTS 6,245,968 B1 * 6/2001 Boudec et al. ............... 800/278
2002/0137214 A1 * 9/2002 Daniell ......................... 435/468

FOREIGN PATENT DOCUMENTS

| WO | WO 99/10513 | * | 3/1999 |
| WO | WO 01/81600 | * | 11/2001 |
| WO | WO-01/81600 A2 | | 11/2001 |
| WO | WO-01/96583 A2 | | 12/2001 |
| WO | WO 2004/015115 | * | 2/2004 |
| WO | WO 2004/05519 A1 | | 7/2004 |

OTHER PUBLICATIONS

Ye, Guang-Ning et al., "Plastid-expressed 5-enoylpyruvylshikimate-3-phosphate synthase genes provide high level glyphosate tolerance in tobacco", The Plant Journal, vol. 25, No. 3, pp. 261-270, (2001).
Lutz, Kerry et al., "Expression of bar in the Plastid Genome Confers Herbicide Resistance," Plant Physiology, vol. 125, pp. 1585-1590, (Apr. 2001).
Carrer, Helaine et al., "Targeted Insertion of Foreign Genes into the Tobacco Plastid Genome without Physical Linkage to the Selectable Marker Gene," Bio/Technology, vol. 13, pp. 791-794, (Aug. 1995).
Hajdukiewicz, Peter T. et al., "Multiple pathways for Cre/lox-mediated recombination in plastids," The Plant Journal, vol. 27, No. 2, pp. 161-170, (2001).
H. Daniell et al., "Marker free transgenic plants: engineering the chloroplast genome without the use of antibiotic selection", Curr. Genet, vol. 39, pp. 109-116, 2001.

* cited by examiner

*Primary Examiner* — Anne Kubelik
(74) *Attorney, Agent, or Firm* — Connolly Bove Lodge & Hutz LLP (57) ABSTRACT

The present invention relates to transplastomic plants free of the selectable marker gene, to a method of obtaining such plants and to the vectors used.

15 Claims, 1 Drawing Sheet

Fig. 1

SEQUENCE LISTING

```
<160> NUMBER OF SEQ ID NOS: 9

<210> SEQ ID NO 1
<211> LENGTH: 26
<212> TYPE: DNA
<213> ORGANISM: Artificial
<220> FEATURE:
<223> OTHER INFORMATION: synthetic primer

<400> SEQUENCE: 1
atgtcaccac aaacagagac taaagc                                26

<210> SEQ ID NO 2
<211> LENGTH: 25
<212> TYPE: DNA
<213> ORGANISM: Artificial
<220> FEATURE:
<223> OTHER INFORMATION: synthetic primer
```

<400> SEQUENCE: 2
catcagggac tcccaagcac actag                                    25

<210> SEQ ID NO 3
<211> LENGTH: 34
<212> TYPE: DNA
<213> ORGANISM: Artificial
<220> FEATURE:
<223> OTHER INFORMATION: synthetic primer

<400> SEQUENCE: 3
gaagcttcca tggcagaagc ggtgatcgcc gaag                           34

<210> SEQ ID NO 4
<211> LENGTH: 42
<212> TYPE: DNA
<213> ORGANISM: Artificial
<220> FEATURE:
<223> OTHER INFORMATION: synthetic primer

<400> SEQUENCE: 4
actagttcta gattatttgc cgactacctt ggtgatctcg cc                  42

<210> SEQ ID NO 5
<211> LENGTH: 25
<212> TYPE: DNA
<213> ORGANISM: Artificial
<220> FEATURE:
<223> OTHER INFORMATION: synthetic primer

<400> SEQUENCE: 5
caacagcatc gcctcctact ttgcg                                    25

<210> SEQ ID NO 6
<211> LENGTH: 25
<212> TYPE: DNA
<213> ORGANISM: Artificial
<220> FEATURE:
<223> OTHER INFORMATION: synthetic primer

<400> SEQUENCE: 6
ttcacggaag ttgaacaatt tctcg                                    25

<210> SEQ ID NO 7
<211> LENGTH: 25
<212> TYPE: DNA
<213> ORGANISM: Artificial
<220> FEATURE:
<223> OTHER INFORMATION: synthetic primer

<400> SEQUENCE: 7
tttgtagaaa actagtgtgc ttggg                                    25

<210> SEQ ID NO 8
<211> LENGTH: 25
<212> TYPE: DNA
<213> ORGANISM: Artificial
<220> FEATURE:
<223> OTHER INFORMATION: synthetic primer

<400> SEQUENCE: 8
ttgctccttt cttttcaaaa cctcc                                    25

<210> SEQ ID NO 9
<211> LENGTH: 30
<212> TYPE: DNA

```
<213> ORGANISM: Artificial
<220> FEATURE:
<223> OTHER INFORMATION: synthetic primer

<400> SEQUENCE: 9
ttatttgccg actaccttgg tgatctcgcc                                               30
```

TRANSPLASTOMIC PLANTS FREE OF THE SELECTABLE MARKER GENE

RELATED APPLICATIONS

This application is a national stage application (under 35 U.S.C. 371) of PCT/EP2006/000731 filed Jan. 3, 2006, which claims benefit of French application 0500052 filed Jan. 5, 2005 and US Provisional application 60/683,563 filed May 23, 2005.

The present invention relates to transplastomic plants free of the selectable marker gene, to a method of obtaining such plants and to the vectors used.

Plant transgenesis consists in introducing into a plant one or more genes originating from various organisms (bacteria, viruses, insects, plants), with the aim of providing it with novel characteristics and of improving certain agronomic or food qualities. The great diversity of genes, associated with the development of the conventional genetic transformation techniques, has resulted in the creation of new plant varieties. In certain cases, due to the introduction of characteristics that confer resistance to a herbicide, to pathogens or to various stresses, crop practices can be facilitated and yields increased. In other cases, the nutritive value of the plant and the content of certain essential compounds can be improved.

Many techniques for obtaining stable transgenic plants consist in introducing the foreign gene into the nuclear genome of the plant. However, the foreign genes integrated into the nuclear chromosomes of the host plant can be dispersed into the wild via pollen. Methods that reduce the risk of transgene dispersion into the environment are, as a result, highly beneficial.

Another means of obtaining transgenic plants is the direct transformation of plastids. Specifically, plastid transformation has many advantages, among which mention may be made of:

Plastid transformation, by which the genes are inserted by double homologous recombination into one or more multiple copies of the circular plastid genome (or plastome) present in each cell, has the advantage of precisely targeting the region of the plastome where it is desired to integrate the gene of interest, by means of plastid sequences positioned on either side of the transgene in the transformation vector. This precise targeting avoids the "positional" effect commonly observed in nuclear transgenesis.

The obtaining of a very large number of copies of the transgene per cell. Specifically, depending on the developmental stage, a leaf cell can contain up to 10 000 copies of a small circular genome of 120 to 160 kilobases, each molecule carrying a large repeat sequence. The plant cells can then be manipulated so as to contain up to 20 000 copies of a gene of interest.

This results in high levels of expression; it being possible for the products of the transgenes to represent more than 40% of the total soluble proteins (De Cosa et al., 2001).

Plastid transformation has the other advantage of greatly limiting the risk of transgene dispersion into the environment. Since the traits encoded in the plastids are not generally transmissible via pollen, the potential risk of transgene transmission to wild species is limited.

Plastid transformation techniques are described in the article McBride et al., 1994, in American U.S. Pat. Nos. 5,451,513; 5,545,817; 5,545,818 and 5,576,198, and also in international patent applications WO 95/16783 and WO 97/32977. Plastid transformation by biolistic was initially carried out in the unicellular alga *Chlamydomonas reinhardtii* (Boynton et al., 1988), and this approach has been extended to tobacco (Svab et al., 1990).

The conventional plastid transformation technique involves the bombardment of leaves with microprojectiles to which the DNA is attached (Svab et al., 1993).

At the current time, stable transformation of the plastids of higher plants is currently carried out only in the tobacco plant *N. tabacum* (Svab and Maliga, 1990; Svab et al., 1993). Some recent progress has however been made with the transformation of plastids from rice (Khan and Maligna, 1999), *Arabidopsis thaliana* (Sikdar et al., 1998), potato (Sidorov et al., 1999), rapeseed (Chaudhuri et al., 1999) and tomato (Ruf et al., 2001). Fertile transplastomic plants have been obtained in the case of tobacco, tomato, potato and soybean (WO 04/053133).

Direct plastid transformation has been used to obtain a good level of tolerance to herbicides or resistance to insects, or alternatively for the production of proteins in large amounts. Thus, overexpression, from the tobacco plastome, of genes for tolerance to herbicides such as glyphosate (Daniell, 1998; WO 99/10513; Ye et al., 2000; W0.01/04331, WO 01/04327) or phosphinothricin (Basta) (Lutz et al., 2001) confers excellent tolerance to these herbicides. Other applications have resulted in the production of transplastomic plants that are tolerant to insects or overproduce therapeutic proteins (McBride et al., 1995; U.S. Pat. No. 5,451,513; Staub et al. (2000); WO 99/10513).

However, one of the main disadvantages of the direct transformation of the plastids of higher plants, such as it is conventionally carried out, is the use of a gene for resistance to an antibiotic as a selectable marker.

The selectable marker generally used for the selection of transplastomic lines is the bacterial gene aadA, expressed under the control of plastidial regulatory elements (Svab et al, 1993; Staub et al, 1993). Expression of the aadA gene, which encodes an aminoglycoside 3'-adenylyltransferase, confers resistance to two antibiotics, spectinomycin and streptomycin. The product of the aadA gene prevents spectinomycin (or streptomycin) from binding to 16S RNA, a component of the 30S subunit of plastidial ribosomes, involved in recognition of the translation initiation codon, and therefore from inhibiting translation within the plastid. Only the cells that contain plastids expressing the product of the aadA gene will be able to continue to grow optimally in vitro and to remain green. An alternative selectable marker is a 16S RNA sequence that has a point mutation that makes it insensitive to spectinomycin.

Unfortunately, this antibiotic also controls bacterial infections in humans and animals. There is, as a result, a great deal of anxiety with regard to the potential risks for health and the environment associated with the presence of a gene for resistance to an antibiotic in transgenic crops. Methods that make it possible to eliminate selectable marker genes, in particular antibiotic marker genes, while at the same time keeping the gene of interest present in the transgenic plant, are therefore of major interest.

A certain number of more or less complex techniques have been described for eliminating a selectable marker gene that is integrated into the chromosomes. If the marker gene is not genetically linked to the gene of interest, one can hope to eliminate it by crossing and analysis of the progeny. When the selectable marker is genetically linked, other techniques such as those based on the use of transposable elements (PCT/US91/04679; Yoder et al 1993) or on the use of site-specific recombination systems such as the cre/lox system of the P1 bacteriophage or the yeast FLP/FRT system (FliPase recombinase; Lyzrik et al., 1997), can be used.

Site-specific recombination has also been applied to the elimination of a transplastomic marker gene by introduction into the nuclear genome of the plant of a second transgene encoding a CRE protein targeted to the chloroplasts by means of its transit peptide (EP1218488)

In *C. reinhardtii* algae, selection methods based on photosynthetic mutants have made it possible to introduce foreign genes of interest into the plastid genome without the use of antibiotic selectable marker genes such as aadA. However, these methods cannot be used in higher plants since they are based on the existence of photosynthetic mutants.

The double homologous recombination phenomenon, which is the basis of plastid genome transformation, can also be used for the subsequent elimination of part of the transgene, in particular of the selectable marker. The principle of this elimination has been described in *Chlamydomonas* (Fischer et al, 1996) and in tobacco (WO 01/81600). The technique used consists in transforming the plastid genome with a nucleic acid sequence comprising the gene of interest and a selectable marker gene bordered by two identical DNA sequences, in the same orientation, and sufficiently long to activate the homologous recombination system. The transformation events are selected by culturing on a first selection medium corresponding to the selectable marker gene used. The calluses are propagated in a selective medium so as to obtain homoplasmic plants in which all the plastid genomes contain the selectable marker gene and the gene of interest. The plants and their progeny are subsequently cultivated in a non-selective medium so as to allow excision of the selectable marker gene.

A system for selecting the plants that have eliminated the marker gene has been used in *Arabidopsis*, but it relates to transformation of the nuclear genome (WO 01/96583). In this method, the plants are transformed using a vector which comprises two copies of the gene of interest in the same orientation, surrounding a positive selectable marker gene and a negative selectable marker gene. The positive selectable marker gene makes it possible to select the events that incorporated the transgene into their genome. The presence of the two copies of the gene of interest makes it possible, by homologous recombination, to eliminate the two (positive and negative) selectable marker genes and also one of the two copies of the gene of interest. The events which have undergone this homologous recombination are then selected by culturing on the negative selectable marker which prevents growth of the cells which still have the corresponding selectable marker gene. An example of such a negative selectable marker gene is CodA (*Escherichia coli* cytosine deaminase), which deaminates 5-fluorocytosine (non-toxic) to 5-fluorouracil, which is toxic.

In the context of the present application, the authors have succeeded in developing a method which includes, in the course of plastid transformation, the selection of the plants that have eliminated the marker gene. This method makes it possible to reliably obtain events that are homoplasmic for the presence of the gene of interest and the absence of the selectable marker, in particular antibiotic selectable marker. This method also has the advantage that the expression of the gene of interest is correlated with and dependent on the elimination of the marker gene, and that this elimination does not leave during the recombination any remaining exogenous DNA other than the gene of interest. This method also has the great advantage, when a selective characteristic is provided by the expression of the gene of interest, of promoting and accelerating the production of plants homoplasmic for the presence of the gene of interest. This is the case, for example, when the gene of interest is a gene for tolerance to herbicides such as isoxaflutoles, glyphosate or phosphinothricin (Basta).

DETAILED DESCRIPTION OF THE INVENTION

A subject of the present invention is a method of obtaining transplastomic plants free of selectable marker, in particular antibiotic selectable marker, comprising at least the following steps:

a) transforming at least one plant cell with a vector suitable for the transformation of plastids, comprising, in the direction of transcription, a sequence (i) corresponding to the 5' portion of a chimeric gene of interest, a chimeric gene (ii) comprising a sequence encoding a selectable marker that confers resistance to a selection agent, a fragment (iii) of n nucleotides that is identical to the 3' portion of the sequence (i), a sequence (iv) corresponding to the remaining 3' portion of the chimeric gene of interest;

b) culturing the cells comprising the transformed plastids on a first medium comprising the selection agent;

culturing the cells on a second medium that does not comprise the selection agent.

It is understood that, according to the invention, the vector used in step a) of the method described above does not comprise the chimeric gene of interest in complete form.

The expression "chimeric gene of interest in complete form" or "complete chimeric gene of interest" is intended to mean a non-truncated sequence of this gene of interest.

In a particular embodiment, n represents at least 25 nucleotides, preferably at least 30, preferably at least 50 nucleotides.

The expression "vector suitable for the transformation of plants" may refer, by way of example, to a transformation vector comprising two regions for homologous recombination of the plastome of the plant, bordering a genetic construction or construct according to the invention.

These regions, located upstream (LHRR) and downstream (RHRR) of the elemental chimeric gene(s), allow double homologous recombination with an intergenic region of the plastome which comprises the contiguous LHRR and RHRR regions.

Preferably, the two homologous recombination regions according to the invention correspond to contiguous sequences that allow the integration of the chimeric gene into an intergenic region of the plastome. In a particular embodiment, this region corresponds to the region of the plastome ribosomal RNA operon. In another particular embodiment, this intergenic region comprises the 3' end of the rbcL gene encoding the Rubisco large subunit, and the other homologous sequence comprises the 5' end of the accD gene, encoding a subunit of acetyl-CoA-carboxylase. In addition, more particularly, this intergenic region comprises the 3' end of the rbcL gene encoding the Rubisco large subunit corresponding to nucleotides 57755 to 59297 of the plastome of *N. tabacum*, cv. Petit Havana, and the other homologous sequence comprises the 5' end of the accD gene corresponding to nucleotides 59298 to 60526 of the plastome of *N. tabacum*, cv. Petit Havana.

The expression "remaining 3' portion of the chimeric gene of interest" is intended to mean the fact that the juxtaposition, in the direction of transcription, of the sequence (i) and of the sequence (iv) reconstitutes the chimeric gene of interest in its entirety.

The expression "chimeric gene of interest" is intended to mean a nucleotide sequence comprising, functionally linked to one another in the direction of transcription, a regulatory promoter sequence that is functional in plastids, a sequence encoding a protein of interest, and a terminator that is functional in the plastids of plant cells.

The expression "chimeric gene comprising a sequence encoding a selectable marker" is intended to mean a nucleotide sequence comprising, functionally linked to one another in the direction of transcription, a regulatory promoter sequence that is functional in plastids, a sequence encoding a selectable marker, and a terminator that is functional in the plastids of plant cells.

The term "chimeric gene" is generally intended to mean a gene for which certain elements are not present in the native gene, but have been substituted for elements present in the native gene or have been added.

According to the invention, the term "chimeric gene" may also correspond to the case where all the elements of the gene are present in the native gene, and alternatively, the term "gene" may correspond to a chimeric gene.

Other elements, such as introns, enhancers, polyadenylation sequences and derivatives, the role of which is to improve the expression or the function of the transforming gene, may also be present in order to improve expression of the gene.

The expression "functionally linked to one another" means that said elements of the elemental chimeric gene are linked to one another in such a way that their function is coordinated and allows the expression of the coding sequence. By way of example, a promoter is functionally linked to a coding sequence when it is capable of ensuring the expression of said coding sequence. The construction of the chimeric gene according to the invention and the assembly of its various elements can be carried out using techniques well known to those skilled in the art, in particular those described in Sambrook et al. (1989, Molecular cloning: A Laboratory Manual, Nolan C. ed., New York: Cold Spring Harbor Laboratory Press). The choice of the regulatory elements constituting the chimeric gene depends essentially on the plant and on the type of plastid in which they must function, and those skilled in the art are capable of selecting regulatory elements that are functional in a given plant.

Among the promoters that are functional in the plastids of plant cells and that can be used to implement the present invention, mention may be made, by way of example, of the promoter of the psbA gene, encoding the D1 protein of PSII (Staub et al., 1993, EMBO Journal 12(2): 601-606) or the constitutive promoter of the ribosomal RNA operon Prrn (Staub et al., 1992, Plant Cell 4: 39-45) or the tobacco Prrn promoter combined with a 5' portion of the 5' untranslated region of the tobacco rbcL gene (Svab et al., 1993, Proc. Natl. Acad. Sci. 90: 913-917). In general, any promoter derived from a plant plastome gene or from a bacterial gene will be suitable, and those skilled in the art are capable of making the appropriate choice from the various promoters available so as to obtain a desired method of expression (constitutive or inducible).

Among the terminators that are functional in the plastids of plant cells, mention may be made, by way of example, of the terminator of the psbA gene, of the rbcL gene encoding the Rubisco large subunit, or of the rps16 gene encoding a ribosomal protein of tobacco (Shinozaki et al., 1986; Staub et al., 1993).

The chimeric gene comprising a sequence encoding a selectable marker makes it possible to select the plastids and the cells that are effectively transformed, i.e. those that have incorporated the chimeric gene(s) into their plastome. The selection of the transformants is accomplished by culturing the transformed cells or tissues on a medium containing the selection agent.

The selectable marker genes commonly used include the genes encoding genes for resistance to antibiotics, herbicides or to other compounds, which may be lethal for the cells, organelles or tissues that do not express the resistance gene or allele. The selection agent is then the corresponding antibiotic, herbicide or selective compound. If said agent is lethal for the cell, only the transformed cells will live and develop on this medium, whereas the non-transformed cells will die. If the selection agent is not lethal for the cell, the transformed cells and the non-transformed cells will be distinguished by virtue of a different behaviour that may be demonstrated.

A selectable marker may be non-lethal at the cellular level but lethal at the organelle level. For example, the antibiotic spectinomycin inhibits mRNA translation to protein in plastids, but not in the cytoplasm. The tissues containing non-resistant plastids will be whitish whereas the tissues containing resistant plastids will be green. In a dividing cell containing transformed plastids and non-transformed plastids, the non-transformed plastids will disappear under the selection pressure, for the benefit of the transformed plastids, and a population of cells comprising only transformed plastids may be obtained.

The expression "selectable marker gene" is intended to mean a gene encoding a selectable marker, or a chimeric gene encoding a selectable marker.

Among the genes encoding selectable markers, that can be used, mention may be made of genes for resistance to the antibiotics spectinomycin-streptomycin and kanamycin, such as, for example, the chimeric genes aadA encoding an aminoglycoside 3"-adenylyltransferase (Svab et al., 1993) and neo encoding a neomycin phosphotransferase (Carrer et al., 1993) respectively, but also a gene for tolerance to betaine aldehyde, such as the gene encoding betaine aldehyde dehydrogenase (Daniell et al., 2001), but also genes for tolerance to herbicides, such as the bar gene (White et al., 1990, Nucleic Acid Res. 18(4):1062) for tolerance to bialaphos, or the EPSPS gene (U.S. Pat. No. 5,188,642) for tolerance to glyphosate. Use may also be made of reporter genes encoding readily identifiable enzymes such as the GUS enzyme (β-glucuronidase) (Staub et al., 1993) or GFP (green fluorescent protein) (Sidorov et al., 1999), or genes encoding pigments or enzymes that regulate the production of pigments in the transformed cells. Such genes are in particular described in patent applications WO 91/02071, WO 95/06128, WO 96/38567, WO 97/04103 and WO 01/64023.

Preferably, the gene encoding the selectable marker is a gene for resistance to an antibiotic. A preferred gene encoding the selectable marker is the aadA gene encoding an aminoglycoside 3"-adenylyltransferase that confers resistance to streptomycin and to spectinomycin (Svab et al., 1993).

According to the invention, the chimeric gene comprising a sequence encoding a selectable marker is flanked on either side by the two fragments of a same chimeric gene of interest, such that the juxtaposition, in the direction of transcription, of these two fragments reconstitutes the chimeric gene of interest. These two fragments are the sequence (i) corresponding to the 5' portion of a chimeric gene of interest and the sequence (iv) corresponding to the remaining 3' portion of the chimeric gene of interest. In addition, a fragment of n nucleotides that is identical to the 3' portion of the sequence (i) is present between the chimeric gene (ii) comprising a sequence encoding a selectable marker and the sequence (iv) corresponding to the remaining 3' portion of the chimeric gene of interest. This fragment of n nucleotides corresponds to the 3' end of the first fragment of the gene of interest flanked at the 5' end of the chimeric gene comprising a sequence encoding a selectable marker, and is duplicated at the 5' end of the second fragment of the gene of interest flanked at the 3' end of the chimeric gene comprising a sequence encoding the selectable marker. In this way, a direct repeat sequence of n nucleotides of the gene of interest frames the chimeric gene comprising a sequence encoding a selectable marker. This identical fragment of n nucleotides must have a size that allows the activation of the homologous recombination system between the two identical fragments flanking the chimeric gene encoding a selectable marker. The homologous recombination between these two identical fragments causes the excision of the chimeric gene comprising a sequence encoding a selectable marker, and also the excision of one of the two identical fragments of n nucleotides, and brings about the reconstitution of a complete and functional chimeric gene of interest, which can then be expressed in the cell.

The construction according to the invention can be carried out using techniques well known to those skilled in the art, in particular those described in Sambrook et al. (1989, Molecular Cloning: *A Laboratory Manual*, Nolan C. ed., New York: Cold Spring Harbor Laboratory Press). It may also be completely or partially synthetic and produced by conventional chemical synthesis techniques.

A direct repeat sequence is a sequence of nucleic acids that is duplicated and the duplicated sequence of which is oriented in the same direction as the original sequence, and not in the opposite direction.

Preferably, the repeat sequence on either side of the chimeric gene comprising a sequence encoding a selectable marker is a sequence of at least 50 nucleotides, more preferably of at least 100 nucleotides.

According to the invention, the term "transplastomic plants" is intended to mean plants that have stably integrated into their plastome a chimeric gene that is functional in plastids, in particular in chloroplasts. The plastome consists of the genome of the cellular organelles other than the nucleus, in particular the chloroplasts genome.

The transformation of the cells can be carried out by any method of transforming plant cells. Among the transformation methods that can be used to obtain transformed cells according to the invention, one of these consists in bringing the cells or tissues of the plants to be transformed into contact with polyethylene glycol (PEG) and with the transformation vector (Chang and Cohen, 1979, Mol. Gen. Genet. 168(1), 111-115; Mercenier and Chassy, 1988, Biochimie 70 (4), 503-517). Electroporation is another method which consists in subjecting the cells or tissues to be transformed and the vectors to an electric field (Andreason and Evans, 1988, Biotechniques 6(7), 650-660; Shigekawa and Dower, 1989, Aust, J. Biotechnol. 3(1), 56-62). Another method consists in directly injecting the vectors into the cells or the tissues by microinjection (Gordon and Ruddle, 1985, Gene 33(2), 121-136). The transformation of plant cells or tissues can also be carried out by means of bacteria of the *Agrobacterium* species, preferably by infection of the cells or tissues of said plants with *A. tumefaciens* (Knopf, 1979, Subcell. Biochem. 6, 143-173; Shaw et al., 1983, Gene 23(3):315-330) or *A. rhizogenes* (Bevan and Chilton, 1982, Annu. Rev. Genet. 16:357-384; Tepfer and Casse-Delbart, 1987, Microbial. Sci. 4(1), 24-28) that have been genetically modified, thus allowing the targeting of the T-DNA specifically to the plastids. Preferably, the transformation of plant cells or tissues with *Agrobacterium tumefaciens* is carried out according to the protocol described by Ishida et al. (1996, Nat. Biotechnol. 14(6), 745-750).

According to a preferred embodiment of the method according to the invention, the method referred to as particle bombardment or biolistic method will be used. It consists in bombarding the tissues with particles onto which the vectors according to the invention are adsorbed (Bruce et al., 1989, Proc. Natl. Acad. Sci. USA 86(24), 9692-9696; Klein et al., 1992, Biotechnology 10(3), 286-291; U.S. Pat. No. 4,945,050).

After transformation, a selection step carried out using a first culture medium comprising the selection agent corresponding to the selectable marker gene used makes it possible to select the transformation events that have integrated the exogenous DNA into the plastid genome. For example, if the aadA gene is used as selectable marker gene, the selection medium used will comprise spectinomycin and/or streptomycin. The material capable of growing on this medium will be propagated and/or regenerated while maintaining this spectinomycin and/or streptomycin selection so as to obtain tissues or plants that contain the exogenous DNA in all the plastid genomes.

In a subsequent step, the cells or tissues selected on the first culture medium are placed in a second medium, referred to as non-selective medium, so as to make it possible to eliminate the gene encoding the selectable marker and to obtain a complete and functional gene of interest by recombination between the repeat sequences. The elimination of the selectable marker can be demonstrated by testing the sensitivity of the cells to the selection agent, and/or by testing the expression of the gene of interest, and/or by using molecular biology techniques such as Southern blotting-type hybridization and the PCR technique.

The term "non-selective medium" is intended to mean a medium that does not contain the selection agent.

The culture media used are well known to those skilled in the art, in particular those described in Gamborg et al. (1968, Exptl Cell Res 50, 151-158) and Murashige et al. (1962, Physiologia Plantarum 15, 473-497).

A "complete and functional gene of interest" denotes a gene of interest capable of being expressed and of encoding a peptide or a functional protein. In addition, according to the invention, it is a gene that has been reconstituted following the excision of the gene encoding a selectable marker by homologous recombination.

The gene of interest may be any gene introduced into the plant so as to confer on it a specific advantage.

According to a particular embodiment of the invention, the gene of interest encodes a peptide or a protein that confers a selective characteristic different from that provided by the selectable marker.

In this particular embodiment, the method of obtaining transplastomic plants according to the invention can advantageously be promoted by means of an additional selection step on a medium comprising a selection agent corresponding to the chimeric gene of interest.

This additional selection step can be carried out jointly with step c) of the method according to the invention, the cells then being cultured on a medium that does not comprise the selection agent corresponding to the selectable marker and that comprises the selection agent corresponding to the chimeric gene of interest.

Alternatively, the selection step on a medium comprising the selection agent corresponding to the chimeric gene of interest is carried out after the step of culturing on a medium that does not comprise the selection agent corresponding to the selectable marker.

In all cases, this additional selection step on a medium comprising the selection agent corresponding to the chimeric gene of interest is carried out after the step (b) of selection on the first medium comprising the selection agent corresponding to the selectable marker.

In this particular embodiment, the method of obtaining transplastomic plants free of the selectable marker, in particular antibiotic selectable marker, comprises at least the following steps:
a) transforming at least one plant cell with a vector suitable for the transformation of plastids, comprising, in the direction of transcription, a sequence (i) corresponding to the 5' portion of a chimeric gene of interest that confers a selective characteristic different from that provided by the selectable marker, a chimeric gene (ii) comprising a sequence encoding a selectable marker that confers resistance to a selection agent, a fragment (iii) of n nucleotides that is identical to the 3' portion of the sequence (i), a sequence (iv) corresponding to the remaining 3' portion of the chimeric gene of interest;
b) culturing the cells comprising the transformed plastids on a first medium comprising the selection agent corresponding to the selectable marker;
c) culturing the cells on a second medium that does not comprise the selection agent corresponding to the selectable marker and that comprises the selection agent corresponding to the chimeric gene of interest.

It is understood that, according to the invention, the vector used in step a) of the method described above does not comprise the chimeric gene of interest in complete form.

In another particular embodiment, a step b') is carried out between step b) and step c), this step b') consisting in culturing the cells on a third medium that comprises neither the selection agent corresponding to the marker gene, nor the selection agent corresponding to the chimeric gene of interest.

The expression "chimeric gene of interest that confers a selective characteristic" is intended to mean a gene of interest that encodes a peptide or a protein that confers a specific characteristic, making it possible to select the cells or plastids that express this peptide or this specific protein by means of a selection agent corresponding to this specific characteristic. Such a gene is generally a gene for resistance to a chemical compound that is lethal for the plant cells.

In general, any gene or group of genes that makes it possible to confer resistance on plant cells with respect to a chemical compound that is lethal for said cells can be used. In addition, the resistance to said chemical compound may consist of a detoxification of said compound by modification of its structure, said modification resulting in the elimination of the lethal effect of said compound. In this case, the gene of interest generally encodes a detoxifying enzyme. Examples of detoxifying enzymes are enzymes for tolerance to bromoxynil or to basta (EP 242 236, EP 337 899). The resistance may also consist of a resistance by insensitization of the target of said compound. In this case, the gene of interest generally encodes a modified functional target, which is made insensitive to said compound by modification of its peptide structure by means of mutations, additions or deletions of specific amino acids. Examples of functional enzymes that are less sensitive to the herbicide or to its active metabolite are the glyphosate-tolerance enzymes (EP 293 356, Padgette S. R. et al, J. BIOL. Chem., 266, 33, 1991; FR 2 736 926). The resistance may also consist of the overexpression of the sensitive enzyme, so as to produce, in the plant, sufficient amounts of target enzyme from the viewpoint of the kinetic constants of this enzyme with respect to the herbicide so as to have sufficient functional enzyme, despite the presence of its inhibitor.

According to a preferred embodiment of the invention, the chimeric gene of interest that confers a selective characteristic is a gene for resistance to a herbicide.

Even more preferably, the chimeric gene of interest that confers a selective characteristic encodes a hydroxyphenylpyruvate dioxygenase (HPPD).

Hydroxyphenylpyruvate dioxygenases (HPPDs) are enzymes that catalyse the reaction of conversion of parahydroxyphenylpyruvate (HPP) to homogentisate (Crouch N. P. & al., Tetrahedron, 53, 20, 6993-7010, 1997).

The term "HPPD" is intended to mean any native, mutated or chimeric HPPD enzyme exhibiting the HPPD activity. Many HPPDs are described in the literature, in particular the HPPDs of bacteria such as *Pseudomonas* (Rüetschi & al., Eur. J. Biochem., 205, 459-466, 1992, WO 96/38567), of plants, for instance *Arabidopsis* (WO 96/38567, Genebank AF047834) or of carrot (WO 96/38567, Genebank 87257), of *Coccicoides* (Genebank COITRP) or of mammals such as humans, mice or pigs.

According to the invention, the term "mutated HPPD" is intended to mean HPPDs mutated so as to obtain properties of tolerance to HPPD-inhibiting herbicides, that are improved compared with the corresponding native HPPD. Advantageously, the mutated HPPD is an HPPD mutated in its C-terminal portion, as described in patent application WO 99/24585. Advantageously, the mutated HPPD comprises the mutation W336 as described in patent application WO 99/24585.

The term "chimeric HPPD" is intended to mean an HPPD comprising elements from various HPPDs, in particular the chimeric HPPDs described in patent application WO 99/24586.

Advantageously, the HPPD is a *Pseudomonas fluorescens* HPPD (WO 96/38567).

Certain molecules that inhibit this enzyme, which attach to the enzyme so as to inhibit the conversion of HPP to homogentisate, are moreover known. Some of these molecules have found a use as herbicides, in so far as inhibition of the reaction in plants results in bleaching of the leaves of the plants treated, and in the death of said plants. (Pallett K. E. et al. 1997 Pestic. Sci. 50 83-84). Such herbicides having HPPD as a target, that are described in the state of the art, are especially isoxazoles (EP 418 175, EP 470 856, EP 487 352, EP 527 036, EP 560 482, EP 682 659, U.S. Pat. No. 5,424, 276), in particular isoxaflutole (IFT), a herbicide selective for maize, diketonitriles or DKNs (EP 496 630, EP 496 631), in particular 2-cyano-3-cyclopropyl-1-(2-$SO_2CH_3$-4-$CF_3$-phenyl)propane-1,3-dione and 2-cyano-3-cyclopropyl-1-(2-$SO_2CH_3$-4-2,3-$Cl_2$-phenyl)propane-1,3-dione, triketones (EP 625 505, EP 625 508, U.S. Pat. No. 5,506,195), in particular sulcotrione or mesotrione, or else pyrazolinates.

According to another preferred embodiment of the invention, the chimeric gene of interest that confers a selective characteristic encodes a 5-enolpyruvylshikimate-3-phosphate synthase (EPSPS).

EPSPS is a plastid enzyme involved in the shikimate biosynthetic pathway, resulting in the synthesis of aromatic amino acids. EPSPS is known to be the target enzyme of herbicides of the family of phosphonic acids of phosphonomethylglycine type.

Sequences encoding EPSPSs which are naturally tolerant, or used as such, with respect to herbicides of the phosphonomethylglycine family, in particular with respect to glyphosate, are known. By way of example of genes encoding tolerant EPSPS enzymes, mention may be made of the sequence of the AroA gene of the bacterium *Salmonella typhimurium* (Comai et al., 1983, Science 221, 370-371), the sequence of the CP4 gene of the bacterium *Agrobacterium* sp. (WO 9210/04449), or the sequences of the genes encoding the EPSPS of Petunia (Shah et al., 1986, Science 233, 478-481), of tomato (Gasser et al., 1988, J. Biol. Chem. 263, 4280-4289) or of *Eleusine* (WO 01/66704).

Sequences encoding EPSPSs that have been made tolerant to glyphosate by mutation are also known. By way of example, mention may be made of the sequences of the genes encoding mutated EPSPSs of bacterial origin (Stalker et al., 1985, J. Biol, Chem. 260(B), 4724-4728) or of plant origin (EP 0293358; Ruff et al., 1991, Plant Physiol. 96(S), Abstract 592; WO 91/04323; WO 92/06201; EP 0837944).

According to another preferred embodiment of the invention, the chimeric gene of interest that confers a selective characteristic is the bar gene, which confers resistance to a herbicide such as phosphinothricin (Basta) (Lutz et al, 2001).

According to the invention, the selectable marker gene is excised by recombination, this excision allowing the reconstitution of the complete chimeric gene of interest, which can then be expressed and produce a functional protein of interest. The selection of the plastids that express the gene of interest is accomplished by culturing the transformed cells or tissues on a medium containing an agent with respect to which the production of this peptide or of this protein confers a selective advantage. When the cells divide, the plastids for which the excision of the selectable marker has not occurred will disappear under the selection pressure, to the benefit of the plastids for which the excision of the selectable marker has occurred, and a population of cells homoplasmic for the presence of the gene of interest and the absence of the selectable marker can be obtained more rapidly than in the absence of selection-based on the reconstitution of the gene of interest.

The expression "homoplasmic plants, cells or tissues" is intended to mean plants, cells or tissues comprising only transformed plastomes, i.e. plants, cells or tissues that do not comprise any wild-type plastids.

The invention also relates to a genetic construction or construct comprising, in the direction of transcription:
a sequence (i) corresponding to the 5' portion of a chimeric gene of interest,
a chimeric gene (ii) comprising a sequence encoding a selectable marker,
a fragment (iii) of n nucleotides that is identical to the 3' portion of the sequence (i),
a sequence (iv) corresponding to the remaining 3' portion of the chimeric gene of interest.

It is understood that, according to the invention, said genetic construction or construct does not comprise the complete chimeric gene of interest. This complete chimeric gene of interest is reconstructed following the excision of the chimeric gene comprising a sequence encoding a selectable marker.

The invention relates to a genetic construction or construct comprising, in the direction of transcription, a sequence (i) corresponding to the 5' portion of a chimeric gene of interest, a chimeric gene (ii) comprising a sequence encoding a selectable marker, a fragment (iii) of n nucleotides that is identical to the 3' portion of the sequence (i), a sequence (iv) corresponding to the remaining 3' portion of the chimeric gene of interest, said sequence (iv) being absent in the position 5' of the sequence (ii).

According to a particular embodiment of the invention, the construct comprises, in the direction of transcription, a sequence (i) corresponding to the 5' portion of a chimeric gene of interest which encodes a peptide or a protein that confers a selective characteristic different from that provided by the selectable marker, a chimeric gene (ii) comprising a sequence encoding a selectable marker, a fragment (iii) of n nucleotides that is identical to the 3' portion of the sequence (i), and a sequence (iv) corresponding to the remaining 3' portion of the chimeric gene of interest.

It is understood, that, according to the invention, said construct does not comprise the complete chimeric gene of interest.

In fact, the sequence (iv) therefore corresponds to the remaining 3' portion of this chimeric gene of interest which encodes a peptide or a protein that confers a selective characteristic different from that provided by the selectable marker. This sequence (iv) is absent in the position 5' of the sequence (ii).

According to a preferred embodiment, the gene of interest is a gene for resistance to a herbicide.

Even more preferably, the chimeric gene of interest encodes a hydroxyphenylpyruvate dioxygenase (HPPD), encodes a 5-enolpyruvylshikimate-3-phosphate synthase (EPSPS), or encodes the bar gene.

The invention also relates to a method of producing a construct, comprising at least the following steps:
a) the introduction of a sequence (ii) comprising a chimeric gene encoding a selectable marker into the sequence encoding a chimeric gene of interest,
b) the duplication, of a fragment (iii) of n nucleotides that is located in the 3' position of the sequence (i) which corresponds to the 5' portion of the chimeric gene of interest that is located in the position 5' of the sequence (ii), in the position 5' of the sequence (iv) which corresponds to the remaining 3' portion of the chimeric gene of interest.

The invention also relates to the construct that can be obtained by means of the method described above.

The invention also relates to a transformation vector suitable for the transformation of plant plastids, characterized in that it comprises a construct according to the invention.

A subject of the invention is also a transplastomic plant cell containing a gene of interest and free of antibiotic selectable marker, that can be obtained by means of one of the methods described above.

A subject of the invention is also transplastomic plants or a part of these plants, and the progeny of these plants, containing a gene of interest and free of antibiotic selectable marker, that can be obtained by means of one of the methods described above.

The molecular biology techniques are described in Ausubel (Ed.), *Current Protocols in Molecular Biology*, John Wiley and Sons Inc. (1994): Maniatis T., Fritsch E. F. and Sambrook J. Molecular Cloning: *A laboratory Manual*, Cold Spring Harbor laboratory, Cold Spring Harbor, N.Y. (1989). The PCR reactions are carried out in a Perkin Elmer GeneAmp PCR system 9600 device. The amplification reactions for each sample are carried out in the course of 30 cycles comprising various steps: a denaturation step at 94° C. for one minute, a pairing step of 45 seconds at a temperature of 50 to 60° C., depending on the primers used, and an elongation step at 72° C. for 1 to 2 minutes depending on the size of the PCR products to be amplified. These cycles are preceded by a denaturation period at 94° C. lasting 5 minutes, and followed by a final elongation period of 5 minutes at 72° C. A temperature of 4° C. is applied after 30 cycles. The PCR products are separated on an agarose gel.

The position of the various DNA fragments derived from the *Nicotiana tabacum* plastome is indicated in accordance with the numbering proposed by Shinozki et al., 1986, and repeated in Genebank under the accession number Z00044.

The invention will be more particularly illustrated by the examples that follow, it being understood that these examples are not limiting.

EXAMPLE 1

Construction of a Plastid Transformation Vector for Eliminating the Marker Gene The plasmid pCLT146 contains the chimeric gene AADA-146 and two incomplete chimeric HPPD-146 genes bordered by two DNA fragments, "RHRR" (right homologous recombination region) and "LHRR" (left homologous recombination region), facilitating the integration of these cassettes into the rbcL-accD region of the tobacco plastid genome. The LHRR fragment corresponding to the 3' end of the rbcL gene encoding the Rubisco large subunit, and the RHRR fragment corresponding to the 5' end of the accD gene, were described in patent FR 2848568-A1.

The plasmid pCLT146 comprises, in the direction of transcription, a sequence (i) HPPD-146a corresponding to the 5' portion of the chimeric gene of interest hppd, a chimeric gene (ii) AADA-146 comprising a sequence encoding a selectable marker, a fragment HPPD-146b comprising the sequence (iii) that is identical to the 3' portion of the sequence (i) and the sequence (iv) corresponding to the remaining 3' portion of the chimeric gene of interest hppd.

Figure 1:
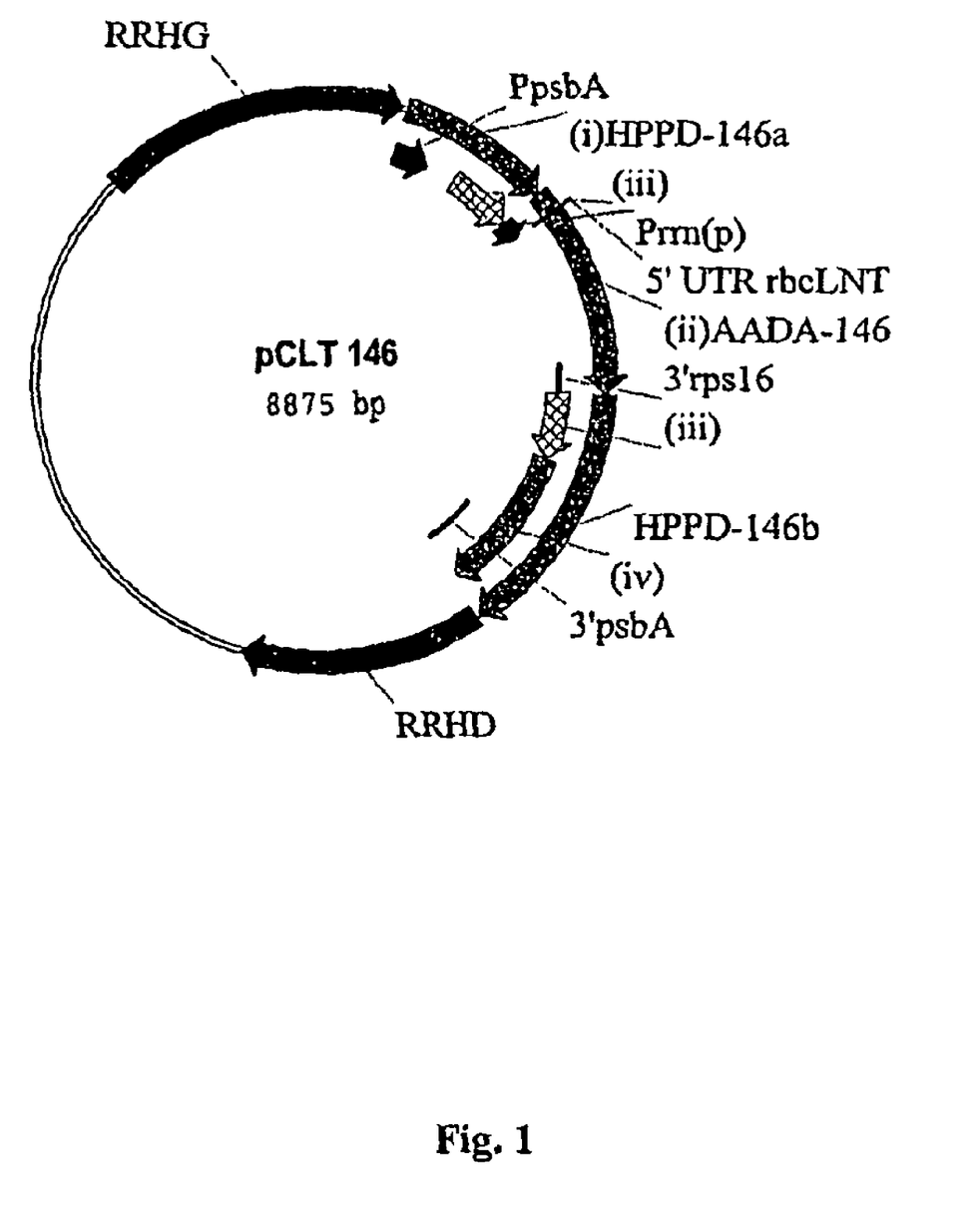
FIG. 1: map of the plasmid pCLT146

The chimeric gene AADA-146 is composed, from 5' to 3', of the promoter of the ribosomal RNA operon ("Prrn", nucleotides 102 564 to 102 680 of the *N. tabacum* plastome), of a portion of the 5' transcribed and untranslated region of the rbcL gene ("5'rbcL", nucleotides 57 577 to 57 594 of the *N. tabacum* plastome), of the coding sequence of the aadA gene, the product of which confers resistance to spectinomycin (Svab and Maliga, 1993), and of the terminator of the rps16 gene ("3'rps16", nucleotides 4930 to 5090 of the *N. tabacum* plastome). It is flanked on either side by two incomplete chimeric genes, HPPD-146a and HPPD-146b. HPPD-146a is located in the position 5' of AADA-146 and comprises, from 5' to 3', the promoter of the psbA gene ("PpsbA", FR 2848568-A1) and the 5' end of the hppd gene of *Pseudomonas fluorescens* (WO 98/02562; sequence 1; nucleotides 1 to 579) (FIG. 1). HPPD-146b is positioned 3' of AADA-146 and comprises, from 5' to 3', a sequence (iii) that is identical to the 3' end of HPPD-146a and corresponds to nucleotides 177 to 579 on the coding region of the hppd gene, and a sequence (iv) corresponding to the remaining 3' portion of the coding sequence of the hppd gene (nucleotides 580 to 1077) and to the terminator of the psbµA gene ("3'psbA", FR 2848568-A1). The presence on either side of the AADA-146 cassette of an identical sequence (iii) as a direct repeat makes it possible to eliminate, by homologous recombination, the chimeric marker gene AADA-146 and to reconstitute the chimeric gene of interest HPPD-146 in its entirety.

EXAMPLE 2

Transformation of Tobacco Plastid Genomes by Biolistics

*Nicotiana tabacum* c.v. 'Petit Havana' plants are cultivated under sterile conditions on an MS medium (Murashige T. and Skoog F., 1962) plus vitamin Gamborg B5 (Kalys M231-1) and sucrose (30 g/l). Leaves of 3 to 5 cm are bombarded on their lower surface using a gun according to the technique of Finer et al. (1992), the "PIG" (particle inflow gun). The gold microprojectiles (particles of 0.6 µm) are complexed with the DNA (5 µg/shot) in the presence of $CaCl_2$ (0.8 to 1 M) and spermidine (14 to 16 mM). The bombarded leaves are then placed so as to position the lower bombarded face on an MS medium supplemented with 0.05 mg/l of α-naphthaleneacetic acid (NAA; Sigma), 2 mg/l of 6-benzylaminopurine (BAP; Sigma), 30 g/l of sucrose and 7 g/l of phytagar (MS 0.05-2 medium). Two to three days after the bombardment, the bombarded leaves are cut into 5 mm-sided squares (as described in patent FR 2848568-A1) and placed still with the lower face on an MS 0.05-2 medium containing 500 mg/l of spectinomycin dihydrochloride. The calluses and the shoots that are resistant to spectinomycin are regenerated on the same medium and are rooted on a medium containing ½ MS, 15 g/l of sucrose and 500 mg/l of spectinomycin, so as to obtain the T0 plants (corresponding to a first regeneration cycle called R1). In order to promote the elimination process, a second regeneration cycle is carried out on an MS 0.05-2 medium without selection agent. The regenerated shoots (called R2 events) are rooted on a medium containing ½ MS, 15 g/l of sucrose and various concentrations of DKN. The TOR1 and TOR2 plants are transferred into a greenhouse. The first generations of seeds (derived from the TOR1 or TOR2 plants) are T1 generations.

EXAMPLE 3

Production and Molecular Analyses of CLT146 Transplastomic Lines

*N. tabacum* (cv. Petit Havana) leaves were bombarded with the pCLT146 plasmids under the experimental conditions described in Example 2. The first step of selection of the transformed calluses was carried out on spectinomycin (500 mg/l) initially (cf. Example 2) 13 spectinomycin-tolerant events (CLT146-1 to -13) were obtained after a 20-shot experiment.

The identification of the transplastomic lines among the 13 tolerant events was carried out by PCR, by designing specific primers to identify the integration of the chimeric genes AADA-146 and HPPD-146 into the plastome. The primers are chosen so as to have a primer that hybridizes in the native plastid genome, adjacent to the point of integration, while the other primer hybridizes to the chimeric gene. The following primers: ORBCL52 (5' atgtcaccacaaacagagactaaagc-3' SEQ ID NO: 1) and psbA176R (5'-catcagggactcccaagcacactag-3' SEQ ID NO: 2), which hybridize respectively to the rbcL gene on the plastome (nucleotides 57595 to 57620) and to the PpsbA promoter of the chimeric gene HPPD-146, were chosen. A PCR product of size corresponding to the expected fragment was observed only in the transplastomic lines and not in the non-bombarded wild-type tobacco plants. The 13 spectinomycin-tolerant events derived from the transformation with pCLT146 all show an insertion of the chimeric genes into the tobacco plastome.

The presence of the two chimeric genes in the transplastomic events was verified by PCR analysis. The primers OAAN5 (5'-gaagcttccatggcagaagcggtgatcgccgaag-3' SEQ ID NO: 3) and OAAXba3 (5'-actagttctagattatttgccgactac-cttggtgatctcgcc-3' SEQ ID NO: 4), which hybridize to the 5' and 3' ends, respectively, of the coding region of the aadA gene, made it possible to amplify a 784 bp PCR product in all the CLT146 transplastomic events. The pair of primers HPPD+(5'-caacagcatcgcctcctactttgcg-3' SEQ ID NO: 5), which hybridizes in the sequence (i) just upstream of the sequence (iii), and HPPD–(5'-ttcacggaagttgaacaatttctcg-3' SEQ ID NO: 6), which hybridizes in the 3' end of the sequence (iii), bring about the amplification, from total DNA, of two expected PCR products: a 1876 by DNA fragment corresponding to the transplastome containing the chimeric gene HPPD-146 disrupted by the chimeric gene AADA-146, and a 373 bp PCR product corresponding to the sequence (iii).

The phenomenon of marker gene elimination by homologous recombination could be demonstrated by PCR using the pair of oligonucleotides psbA230F (5'-tttgtagaaaactagtgtgct-tggg-3' SEQ ID NO: 7) and 3'psbA (5'-ttgctcctttcttttcaaaac-ctcc-3' SEQ ID NO: 8) which bind, respectively, to the PpsbA promoter and the 3'psbA terminator. Two PCR products were observed: a 2689 by DNA fragment corresponding to the transplastome containing the chimeric gene HPPD-146 disrupted by the AADA-146 gene, and a 1186 bp PCR product corresponding to the transplastome having potentially eliminated the chimeric gene AADA-146 by homologous recombination and reconstituted the hppd gene.

EXAMPLE 4

Elimination of the Selectable Marker Gene in the CLT146 Transplastomic Lines and Evaluation of the Tolerance to DKN In Vitro of the Transplastomic Lines The initial selection of the transplastomic events having integrated the chimeric gene AADA-146 is carried out on a medium containing spectinomycin. Pieces of leaves from each TOR1 transplastomic plant regenerated on spectinomycin were cut up and placed on an MS 0.05-2 regeneration medium without selection agent for approximately one month. The latter step makes it possible to regenerate transplastomic plants (TOR2) in which the transgenic plastomes have not only eliminated, in the course of cell divisions, AADA-146 by homologous recombination, but have acquired a reconstituted and functional chimeric hppd gene. The tolerance of the TOR2 transplastomic plantlets of various lines was then evaluated, in vitro, by pricking out on a rooting medium containing 1 ppm of DKN. For each transplastomic line tested, some plantlets are completely tolerant to 1 ppm DKN, unlike the wild-type plants. These plants remain green and show growth and normal rooting. No symptom of phytotoxicity is observed.

EXAMPLE 5

Tolerance to DKN in the T1 Progeny of the TOR1 Transplastomic Plants

Approximately 500 seeds of the CLT146-1, -2, -3 events corresponding to the T1 generations, collected from self-pollinated TOR1 transplastomic plants, are sown onto MS1/21/2 germination media in the presence of 10 ppm DKN. Plantlets exhibiting a normal green phenotype were obtained and therefore possess plastids in which the chimeric gene AADA-146 has been eliminated.

EXAMPLE 6

Western Blotting Analyses of the CLT146 Transplastomic Plants

With the aim of detecting HPPD protein reconstituted after elimination, protein extracts of leaves derived from wild-type, and CLT146-1 and -2 transplastomic tobacco plants (T0) were separated on an acrylamide gel under denaturing conditions, transferred onto a nitrocellulose membrane and incubated with a monoclonal anti-HPPD primary antibody specific for P. fluorescens HPPD. The Western blotting analysis shows a band of 25 approximately 40 kDa, of size identical to the purified reference HPPD protein, present in the CLT146 extracts, but not revealed in the wild-type tobacco protein extract.

The Western blotting analyses and the DKN-tolerance tests demonstrate that the elimination of the aadA marker gene has clearly taken place by homologous recombination, resulting in the production of reconstituted and functional HPPD proteins in the CLT146 transplastomic lines.

EXAMPLE 7

Southern Blotting Analyses of the CLT146 Transplastomic Plants of Generations T0 and T1

The total genomic DNA was isolated from leaves of wild-type tobacco, of CLT146 events of generation T0 (CLT146-1 and CLT146-2), of plants of generation T1 derived from CLT146-1 and 146-2 selected, in vitro, for their good tolerance to the herbicide DKN (T1S 1a, 1b, 1c, 2a, 2b and 2c), and also from plants of generation T1 (T1SR) derived from CLT146-1 and CLT146-2, selected, in vitro, for their good tolerance to the herbicide DKN and then regenerated a second time in the presence of the herbicide.

The genomic DNA was digested with the SacI and XhoI enzymes, separated on an agarose gel, and then transferred onto a nitrocellulose membrane. This membrane was then hybridized with a P32-labelled radioactive probe covering the duplicated region of hppd (nucleotides 177 to 579) repeated on either side of the aadA gene selection cassette.

Visualization of the autoradiogram shows no signal for the wild-type tobacco extract, as expected. For the 2 events of generation T0 (CLT146-1 and CLT146-2), two major bands (2.5 kb and 4.7 kb) are observed, corresponding to the two fragments expected when all the elements of the construct are integrated into the recombinant plastome. A band of weaker intensity (5.7 kb) is observed from this stage, and corresponds to the recombination of the two duplicated hppd fragments. In certain plants of the T1 generation (CLT146-2b and CLT146-2d, for example), the presence of a single band revealed with the P1 probe is observed, only for plants regenerated a second time in the presence of the herbicide DKN (T1SR). This corresponds to complete elimination of the marker gene for the plants regenerated a second time, in vitro, in the presence of the herbicide, this occurring from the T1 generation.

EXAMPLE 8

Molecular Analysis of Plants of Generation T1 and T2 and Phenotypic Analysis of Plants of Generation T2

The DNA of 10 to 20 plantlets derived from seedlings of wild-type tobacco, of the CLT146-2 event (generation T0), and of the CLT146-2d and CLT146-2c plants (generation T1SR; plants regenerated in vitro) was extracted and analysed by PCR so as to use the most sensitive method for verifying the possible residual presence of copies of the aadA marker gene. The primers used (5'-gaagcttccatggcagaagcggt-gatcgccgaag-3' SEQ ID NO: 3 and 5'-ttatttgccgactaccttggt-gatctcgcc-3' SEQ ID NO: 9) make it possible to amplify a 784 by fragment in the presence of the aadA gene.

This analysis clearly shows the presence of the aadA gene in the progeny of the CLT-146-2 event. On the other hand, no signal is detected in the progeny of the CLT146-2c and CLT146-2d plants, demonstrating the complete elimination of the marker gene in the T2 generation.

The in vitro analysis of the phenotype shows that the plantlets derived from the progeny of the CLT146-2b, CLT146-2c and CLT146-2d plants are 100% sensitive to spectinomycin, and 100% resistant to the herbicide DKN.

These results show a complete and rapid elimination of the marker gene, which is effective from the T2, or even T1, generation.

BIBLIOGRAPHY

Andreason and Evans, *Biotechniques* 6(7) (1988), 650-660
Bevan and Chilton, *Annu. Rev. Genet.* 16: (1982), 357-384
Boynton J. E., Gillham N. W., Harris E. H., Hosler J. P., Jones A. R., Randolph-Anderson B. L., Robertson D., Klein T. M., and Shark K. B. *Science* 240 (1988), 1534-1538
Bruce et al, *Proc. Natl. Acad. Sei. USA* 86(24), (1989) 9692-9696
Carrer H. et al. *Mol. Gen. Genet.* 241: (1993), 49-56
Chang and Cohen, *Mol. Gen. Genet.* 168(1) (1979), 111-115
Chaudhuri S. (1999). WO 00/39313
Comai et al, *Science* 221: (1983), 370-371
Crouch et al, *Tetrahedron*, (1997), 53, 20, 6993-7010
Daniell H., Datta R., Varma S., Gray S., and Lee S. B. *Nat. Biotechnol.* 16 (4): (1998) 345-348
Daniell H. et al. *Curr Genet.* 39: (2001) 109-116
De Cosa B., Moar W., Lee S. B., Miller M., and Daniell H. *Nat. Biotechnol.* 19 (1): (2001). 71-74
Fischer N., Stampacchia O., Redding K., and Rochaix J. D. *Mol. Gen. Genet.* 251: (1996). 373-380
Gasser-et al, *J. Biol. Chem.,* 263: (1988), 4280-4289
Gamborg et al, *Exptl Cell Res* 50, (1968), 151-158
Gordon and Ruddle, *Gene* 33(2), (1985), 121-136
Ishida et al, *Nat. Biotechnol.* 14(6), (1996), 745-750
Khan M. S, and Maliga P. *Nat. Biotechnol.* 17, (1999). 910-915
Klein et al, *Biotechnology* 10(3), (1992), 286-291
Knopf, *Subcell. Biochem.* 6, (1979), 143-173
Lutz K. A., Knapp J. E., and Maliga P. *Plant Physiol.* 125(4): (2001), 1585-1590
McBride K. E., Svab Z., Schaaf D. J., Hogan P. S., Stalker D. M., and Maliga P. *Biotechnology* 13(4): (1995). 362-365
Murashige et al, *Physiologia Plantarum* 15, (1962), 473-497
Mercenier and Chassy, *Biochimie* 70(4), (1988), 503-517
Padgette S. R. et al, *J. Biol. Chem.,* 266: (1991), 33
Pallett et al, *pestc. Sci.* 50: (1997), 83-84.
Rüetschi et al, *Eur. J. Biochem.* 205, (1992), 459-466
Ruf et al, *Plant Physiol.* 96(S) (1991), Abstract 592
Ruf S., Hermann M., Berger I. J., Carrer H., and Bock R. *Nat. Biotechnol.* 19(9): (2001). 870-875
Shah et al, *Science* 233: (1986), 478-481
Shaw et al, *Gene* 23(3): (1983), 315-330
Shigekawa and Dower, Aust. *J. Biotechnol.* 3(1), (1989), 56-62
Shinozaki K., Ohme M., Tanaka M., Wakasugi T., Hayashida N., Matsubayashi T., Zaita N., Chunwongse J., Obokata J., Yamaguchi-Shinozaki K., Ohto C., Torasawa K., Meng B. Y., Sugita M., Deno H., Kamogashira T., Yamada K., Kusuda J., Takaiwa F., Kato A., Tohdoh N., Shimada H., and Suguiara M. *EMBO J.* 5: (1986). 2043-2049
Sidorov V. A., Kasten D., Pang S. Z., Hajdukiewicz P. T., Staub J. M., and Nehra N. S. *Plant J.* 19(2): (1999). 209-216
Sikdar S. R., et al. *Plant Cell Reports* 18: (1998). 20-24
Stalker et al, *J. Biol. Chem.* 260(8), (1985), 4724-4728
Staub et al, *Plant Cell* 4: (1992), 39-45
Staub et al, *EMBO Journal* 12(2): (1993), 601-606
Staub J. M., Garcia B., Graves J., Hajdukiewicz P. T., Hunter P., Nehra N., Paradkar V., Schlitter M., Carroll J. A., Spatola L., Ward D., Ye G., and Russell D. A. *Nat. Biotechnol.* 18(3): (2000). 333-338
Svab Z., Hajdukiewicz P., and Maliga P. *Proc. Natl. Acad. Sci. USA* 87(21): (1990). 8526-8530
Svab et al, *Proc. Natl. Acad. Sci.* 90: (1993), 913-917
Tepfer and Casse-Delbart, *Microbiol. Sci.* 4(1), (1987), 24-28
White et al, *Nucleic Acid Res.* 18(4): (1990), 1062
Ye G. N., Hajdukiewicz P. T., Broyles D., Rodríguez D., Xu C. W., Nehra N., and Staub J. M. *Plant J.* 25(3): (2001). 261-270
Yoder et al, 1993
Lyzrik et al, 1997

The invention claimed is:

1. A method of obtaining a transplastomic plant free of a selectable marker gene, said method comprising the following steps:
   a) transforming at least one plant cell with a vector suitable for the transformation of plastids, said vector comprising, in the direction of transcription,
      a sequence (i) corresponding to the 5' portion of a chimeric gene of interest,
      a chimeric gene (ii) comprising a sequence encoding a selectable marker that confers resistance to a selection agent,
      a fragment (iii) of at least twenty-five nucleotides that is identical to the 3' portion of the sequence (i), and
      a sequence (iv) corresponding to the remaining 3' portion of the chimeric gene of interest,
      wherein neither sequence (i) and fragment (iii) nor fragment (iii) and sequence (iv) form a complete chimeric gene of interest;
   b) culturing the cells comprising the transformed plastids transformed cells from step a) on a first medium comprising the selection agent; and
   c) culturing the cells on a second medium that does not comprise the selection agent.

2. The method of obtaining a transplastomic plant free of the selectable marker gene, according to claim 1, characterized in that the chimeric gene of interest that confers a selective characteristic different from that provided by the selectable marker, and in that the second medium used in step c) allows selection of cells expressing said chimeric gene of interest.

3. The method of obtaining a transplastomic plant free of the selectable marker gene, according to claim 2, characterized in that the method comprises an additional step, between step b) and step c), of culturing the cells comprising the transformed plastids on a third medium that comprises neither the selection agent corresponding to the selectable marker, nor the selection agent corresponding to the chimeric gene of interest.

4. The method according to claim 1, in which the selectable marker confers resistance to an antibiotic.

5. The method according to claim 1, in which the sequence encoding a selectable marker encodes an aminoglycoside 3-adenylyltransferase.

6. The method according to claim 1, in which the selectable marker confers resistance to betaine aldehyde.

7. The method according to claim 1, in which the gene of interest encodes a protein that confers resistance to a herbicide.

8. The method according to claim 1, in which the gene of interest encodes a hydroxyphenylpyruvate dioxygenase (HPPD).

9. The method according to claim 1, in which the gene of interest encodes a 5-enol pyruvylshikimate-3-phosphate synthase (EPSPS).

10. The method according to claim 1, in which the gene of interest is the bar gene.

11. A construct comprising, in the direction of transcription:
   a sequence (i) corresponding to the 5' portion of a chimeric gene of interest,
   a chimeric gene (ii) comprising a sequence encoding a selectable marker,
   a fragment (iii) of at least twenty-five nucleotides that is identical to the 3' portion of the sequence (i), and
   a sequence (iv) corresponding to the remaining 3' portion of the chimeric gene of interest,
   wherein neither sequence (i) and fragment (iii) nor fragment (iii) and sequence (iv) form a complete chimeric gene of interest.

12. The construct according to claim 11, in which the sequence (i) corresponds to the 5' portion of a chimeric gene of interest which encodes a protein or a peptide that confers a selective characteristic different from that provided by the selectable marker.

13. A transformation vector suitable for the transformation of plant plastids, characterized in that it comprises a construct according to claim 11.

14. A transplastomic plant cell containing a gene of interest and free of selectable marker, that can be obtained by means of the method according to claim 1.

15. A transplastomic plant or a part of this plant, or the progeny of this plant, containing a gene of interest and free of selectable marker, that can be obtained by means of the method according to claim 1.

\* \* \* \* \*